United States Patent
Hu et al.

(10) Patent No.: US 6,989,448 B2
(45) Date of Patent: *Jan. 24, 2006

(54) HETEROARYL ALKYL ALPHA SUBSTITUTED PEPTIDYLAMINE CALCIUM CHANNEL BLOCKERS

(76) Inventors: Lain-Yen Hu, 4881 S. Ridgeside Cir., Ann Arbor, MI (US) 48105; Michael Francis Rafferty, 3711 Rolling Ridge Ct., Ann Arbor, MI (US) 48105; Todd Robert Ryder, 521 N. Ashley St., Ann Arbor, MI (US) 48103; Anthony Denver Sercel, 2724 Nixon Rd., Ann Arbor, MI (US) 48105; Yuntao Song, 4065 Spring Lake Blvd., Ann Arbor, MI (US) 48108

( * ) Notice: Subject to any disclaimer, the term of this patent is extended or adjusted under 35 U.S.C. 154(b) by 0 days.

This patent is subject to a terminal disclaimer.

(21) Appl. No.: 10/254,416

(22) Filed: Sep. 25, 2002

(65) Prior Publication Data

US 2003/0060419 A1 Mar. 27, 2003

Related U.S. Application Data

(62) Division of application No. 09/663,603, filed on Sep. 18, 2000, now Pat. No. 6,469,038, which is a division of application No. 09/264,193, filed on Mar. 8, 1999, now Pat. No. 6,166,052.

(60) Provisional application No. 60/077,522, filed on Mar. 11, 1998.

(51) Int. Cl.
  C07D 401/00 (2006.01)
  C07D 211/08 (2006.01)
  A61K 31/445 (2006.01)
  A61K 31/47 (2006.01)

(52) U.S. Cl. .................. 546/194; 546/193; 546/192; 546/207; 514/318; 514/326; 514/331; 514/317

(58) Field of Classification Search .......... 546/194, 546/193, 192, 207; 514/318, 326, 331, 317
See application file for complete search history.

(56) References Cited

U.S. PATENT DOCUMENTS

| | | | |
|---|---|---|---|
| 4,791,102 A | * 12/1988 | Bernat et al. ............ | 514/19 |
| 5,232,929 A | 8/1993 | Desai et al. ............. | 514/314 |
| 5,332,817 A | 7/1994 | Desai et al. ............. | 546/16 |
| 5,420,297 A | 5/1995 | Matsuo et al. ............ | 548/525 |
| 5,936,065 A | * 8/1999 | Arrhenius et al. ........ | 530/331 |
| 6,117,841 A | * 9/2000 | Hu et al. ................. | 514/19 |

FOREIGN PATENT DOCUMENTS

| | | |
|---|---|---|
| WO | 92/02501 | 2/1992 |
| WO | 92/02502 | 2/1992 |
| WO | 93/01170 | 1/1993 |
| WO | 93/15052 | 8/1993 |
| WO | 93/15073 | 8/1993 |
| WO | 93/15080 | 8/1993 |
| WO | 93/22302 | 11/1993 |
| WO | 94/13291 | 6/1994 |
| WO | 94/14786 | 7/1994 |
| WO | 95/04027 | 2/1995 |
| WO | 95/11238 | 4/1995 |
| WO | 95/11240 | 4/1995 |
| WO | 95/12612 | 5/1995 |
| WO | 95/13817 | 5/1995 |
| WO | 95/24390 | 9/1995 |
| WO | 95/26327 | 10/1995 |
| WO | 95/33722 | 12/1995 |
| WO | 95/33723 | 12/1995 |
| WO | 96/02494 | 2/1996 |
| WO | 96/21641 | 7/1996 |
| WO | 97/10210 | 3/1997 |
| WO | 97/23216 | 7/1997 |

OTHER PUBLICATIONS

Chemical Abstract 127:51005, Horwell, et al.
Chemical Abstract 120:45970, Woodruff.
Chemical Abstract 119:117788, Boden, et al.

* cited by examiner

Primary Examiner—D. Margaret Seaman

(57) ABSTRACT

The present invention provides compounds that block calcium channels having the Formula I shown below.

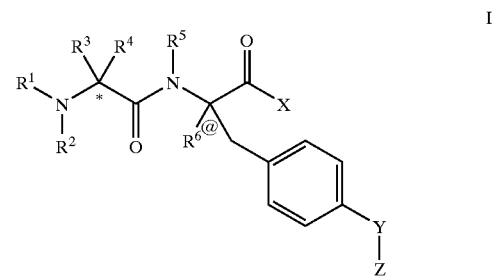

I

The present invention also provides methods of using the compounds of Formula I to treat stroke, cerebral ischemia, head trauma, asthma, amyotropic lateral sclerosis, or epilepsy and to pharmaceutical compositions that contain the compounds of Formula I.

11 Claims, No Drawings

HETEROARYL ALKYL ALPHA SUBSTITUTED PEPTIDYLAMINE CALCIUM CHANNEL BLOCKERS

CROSS REFERENCE TO RELATED APPLICATIONS

This application is a divisional of U.S. Ser. No. 09/663,603, filed Sep. 18, 2000, now U.S. Pat. No. 6,469,038 which is a divisional of U.S. Ser. No. 09/264,193, filed Mar. 8, 1999, now U.S. Pat. No. 6,166,052, and claims benefit of priority from U.S. Provisional Application 60/077,522, filed Mar. 11, 1998.

FIELD OF THE INVENTION

The present invention relates to compounds that act to block calcium channels; methods of using the compounds to treat stroke, cerebral ischemia, pain, head trauma, asthma, amyotropic lateral sclerosis, or epilepsy; and to pharmaceutical compositions that contain the compounds of the present invention.

BACKGROUND OF THE INVENTION

The entry of excessive amounts of calcium ions into neurons following an ischemic episode or other neuronal trauma has been well-documented. Uncontrolled high concentrations of calcium in neurons initiates a cascade of biochemical events that disrupts normal cellular processes. Among these events are the activation of proteases and lipases, breakdown of neuronal membranes, and the formation of free radicals, which may ultimately lead to cell death. Several types of calcium channels have been discovered and called the L, N, P, Q, R, and T types. Each type possesses distinct structural features, functional properties, and cellular/subcellular distributions. Type selective calcium channel blockers have been identified. For example, SNX-111 has been shown to be a selective N-type calcium channel blocker and has demonstrated activity in a number of models of ischemia and pain (Bowersox S. S. et al., *Drug News and Perspective*, 1994:7:261–268 and references cited therein). The compounds of the present invention are calcium channel blockers that can block N-type calcium channels and can be used to treat stroke, pain, cerebral ischemia, head trauma, asthma, amyotropic lateral sclerosis, and epilepsy.

SUMMARY OF THE INVENTION

The present invention provides compounds having the Formula I

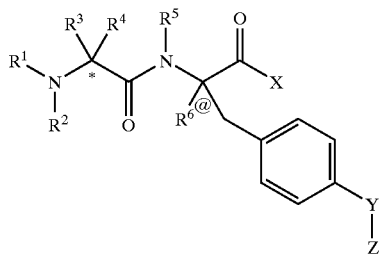

wherein
* denotes a first chiral center when $R^3$ and $R^4$ are different;
@ denotes a second chiral center;
$R^1$ and $R^2$ are independently hydrogen, $C_1$–$C_8$alkyl, $C_3$–$C_7$cycloalkyl, $C_1$–$C_8$substituted alkyl, $C_1$–$C_6$alkoxy, hydroxy, $C_3$–$C_7$cycloalkenyl, $C_3$–$C_7$substituted cycloalkenyl, $C_3$–$C_7$substituted cycloalkyl, —$(CH_2)_n$-aryl, —$(CH_2)_n$-substituted aryl, $C_2$–$C_8$alkenyl, $C_2$–$C_8$substituted alkenyl, —$(CH_2)_n$-heteroaryl, —$(CH_2)_n$-substituted heteroaryl, —$(CH_2)_n$—$C_3$–$C_7$cycloalkyl, —$(CH_2)_n$—$C_3$–$C_7$heterocycloalkyl, —$(CH_2)_n$-substituted $C_3$–$C_7$heterocycloalkyl, or $R^1$ and $R^2$ may be taken together to form a 5- to 7-membered ring which may contain a heteroatom, provided that $R^1$ and $R^2$ are not both hydrogen;

$R^3$, $R^5$, and $R^6$ are independently hydrogen or $C_1$–$C_8$alkyl;

$R^4$ is —$(CH_2)_n$-heteroaryl or —$(CH_2)_n$-substituted heteroaryl;

Y is —$(CH_2)_n$—, —$O(CH_2)_n$—, —$(CH_2)_nO$—, —$N(R^7)(CH_2)_n$—, —$(CH_2)_nN(R^7)$—, —$S(CH_2)_n$—, —$(CH_2)_nS$—, —C=C—, or —C≡C—;

$R^7$ is hydrogen, methyl, or ethyl;

Z is aryl, substituted aryl, heteroaryl, substituted heteroaryl, $C_3$–$C_7$cycloalkyl, substituted $C_3$–$C_7$cycloalkyl, $C_1$–$C_8$alkyl, —$C_3$–$C_7$heterocycloalkyl, or substituted $C_3$–$C_7$heterocycloalkyl;

X is $OR^8$, $NHR^8$, or $NR^8R^9$;

$R^8$ and $R^9$ are independently $C_1$–$C_{12}$alkyl, $C_1$–$C_2$substituted alkyl, —$(CH_2)_n$—$C_3$–$C_8$heterocycloalkyl, $C_3$–$C_7$cycloalkyl, substituted $C_3$–$C_7$cycloalkyl, arylalkyl, substituted arylalkyl, heteroarylalkyl, substituted heteroarylalkyl, or $NR^8R^9$ can together with the nitrogen atom form a ring having from 4 to 7 atoms;

each n is 0 to 5, and the pharmaceutically acceptable salts, esters, amides, and prodrugs thereof.

In a preferred embodiment of the compound of Formula I, $R^1$ is 3-methylbutyl.

In another preferred embodiment of the compounds of Formula I, $R^3$, $R^5$, and $R^6$ are hydrogen.

In another preferred embodiment of the compounds of Formula I,

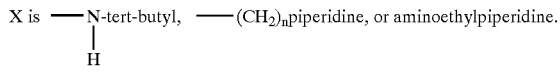

In another preferred embodiment of the compounds of Formula I,

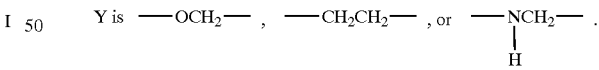

In another preferred embodiment of the compounds of Formula I, Z is phenyl.

In another preferred embodiment of the compounds of Formula I,
$R^1$ is 3-methylbutyl;
$R^3$, $R^5$, and $R^6$ are hydrogen;
$R^4$ is —$CH_2$pyridyl;

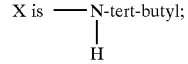

Y is —$OCH_2$—; and
Z is phenyl.

In another preferred embodiment of the compounds of Formula I,
$R^5$ and $R^6$ are hydrogen.

In another preferred embodiment of the compounds of Formula I,
$R^2$ is $C_1$–$C_8$alkyl, cyclohexyl, substituted cyclohexyl, —$CH_2$-phenyl, or $CH_2$-substituted phenyl.

In another preferred embodiment of the compounds of Formula I,

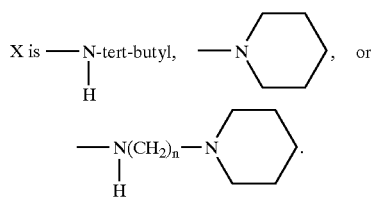

In another preferred embodiment of the compounds of Formula I,
$R^2$ is $C_3$–$C_7$cycloalkenyl.

In another more preferred embodiment of the compounds of Formula I,
$R^1$ is 3-methylbutyl;
$R^2$ is $C_1$–$C_8$ alkyl, substituted cyclohexyl, cyclohexyl, cyclohexenyl, —$CH_2$-phenyl, —$CH_2$-substituted phenyl, —$CH_2$-cyclohexyl, $C_1$–$C_8$alkenyl, —$CH_2$-pyridyl;
$R^3$, $R^5$, and $R^6$ are hydrogen;
$R^4$ is —$CH_2$pyridyl;

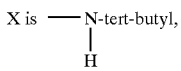

—$(CH_2)_n$piperidine, or aminoethylpiperidine;
Y is —O—$CH_2$—; and
Z is phenyl.

In another more preferred embodiment of the compounds of Formula I,

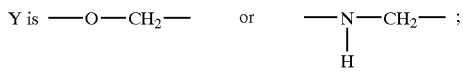

Z is phenyl;

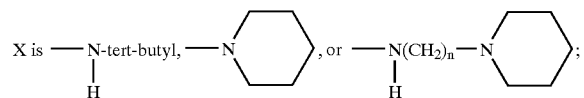

$R^3$ and $R^5$ are hydrogen;
$R^4$ is —$CH_2$pyridyl;
$R^1$ is 3-methylbutyl; and
$R^2$ is $C_1$–$C_8$alkyl, —$(CH_2)_n$substituted phenyl, or cyclohexyl.

In a most preferred embodiment of the present invention, the compounds are:
[S—(R*,R*)]—N-[2-(4-Benzyloxy-phenyl)-1-tert-butylcarbamoyl-ethyl]-2-(3-methyl-butylamino)-3-pyridin-4-yl-propionamide;
[S—(R*,R*)]—N-[2-(4-Benzyloxy-phenyl)-1-tert-butylcarbamoyl-ethyl]-2-(cyclohex-2-enylamino)-3-pyridin-4-yl-propionamide;
[S—(R*,R*)]—N-[2-(4-Benzyloxy-phenyl)-1-tert-butylcarbamoyl-ethyl]-2-(3-methyl-butylamino)-3-pyridin-3-yl-propionamide;
[S—(R*,R*)]—N-[2-(4-Benzyloxy-phenyl)-1-tert-butylcarbamoyl-ethyl]-2-(cyclohex-2-enylamino)-3-pyridin-3-yl-propionamide;
[S—(R*,R*)]—N-[2-(4-Benzyloxy-phenyl)-1-tert-butylcarbamoyl-ethyl]-2-(3-methyl-butylamino)-3-thiazol-4-yl-propionamide;
[S—(R*,R*)]—N-[2-(4-Benzyloxy-phenyl)-1-tert-butylcarbamoyl-ethyl]-2-(cyclohex-2-enylamino)-3-thiazol-4-yl-propionamide;
[S—(R*,R*)]—N-[2-(4-Benzyloxy-phenyl)-1-tert-butylcarbamoyl-ethyl]-2-cyclohexylamino-3-thiazol-4-yl-propionamide;
[S—(R*,R*)]—N-[2-(4-Benzyloxy-phenyl)-1-tert-butylcarbamoyl-ethyl]-2-(cyclohexylmethyl-amino)-3-(1H-imidazol-4-yl)-propionamide;
[S—(R*,R*)]—N-[2-(4-Benzyloxy-phenyl)-1-tert-butylcarbamoyl-ethyl]-2-(1-methylethyl-amino)-3-(1H-imidazol-4-yl)-propionamide;
[S—(R*,R*)]—N-[2-(4-Benzyloxy-phenyl)-1-tert-butylcarbamoyl-ethyl]-2-(cyclohexyl-methyl-amino)-3-pyridin-4-yl-propionamide;
N-[2-(4-Benzyloxy-phenyl)-1-tert-butylcarbamoyl-ethyl]-2-(isobutyl-methyl-amino)-3-pyridin-4-yl-propionamide;
N-[2-(4-Benzyloxy-phenyl)-1-tert-butylcarbamoyl-ethyl]-2-[(3,3-dimethyl-butyl)-methyl-amino]-3-pyridin-4-yl-propionamide;
N-[2-(4-Benzyloxy-phenyl)-1-tert-butylcarbamoyl-ethyl]-2-[methyl-(3-methyl-butyl)-amino]-3-pyridin-4-yl-propionamide;
N-[2-(4-Benzyloxy-phenyl)-1-tert-butylcarbamoyl-ethyl]-2-(cyclohex-2-enyl-methyl-amino)-3-pyridin-4-yl-propionamide;
N-[2-(4-Benzyloxy-phenyl)-1-tert-butylcarbamoyl-ethyl]-2-[(4-dimethylamino-benzyl)-methyl-amino]-3-pyridin-4-yl-propionamide;
N-[2-(4-Benzyloxy-phenyl)-1-tert-butylcarbamoyl-ethyl]-2-[(4-methoxy-benzyl)-methyl-amino]-3-pyridin-4-yl-propionamide;
N-{1-tert-Butylcarbamoyl-2-[4-(3,3-dimethyl-butyl)-phenyl]-ethyl}-2-(3-methyl-butylamino)-3-pyridin-4-yl-propionamide;
N-{1-tert-Butylcarbamoyl-2-[4-(3,3-dimethyl-butyl)-phenyl]-ethyl}-2-[methyl-(3-methyl-butyl)-amino]-3-pyridin-4-yl-propionamide;
N-{1-tert-Butylcarbamoyl-2-[4-(pyridin-2-ylmethoxy)-phenyl]-ethyl}-2-(3-methyl-butylamino)-3-pyridin-4-yl-propionamide;
N-{1-tert-Butylcarbamoyl-2-[4-(pyridin-2-ylmethoxy)-phenyl]-ethyl}-2-[methyl-(3-methyl-butyl)-amino]-3-pyridin-4-yl-propionamide;
N-{1-tert-Butylcarbamoyl-2-[4-(pyridin-3-ylmethoxy)-phenyl]-ethyl}-2-(3-methyl-butylamino)-3-pyridin-4-yl-propionamide;
N-{1-tert-Butylcarbamoyl-2-[4-(pyridin-3-ylmethoxy)-phenyl]-ethyl}-2-[methyl-(3-methyl-butyl)-amino]-3-pyridin-4-yl-propionamide;
N-[2-(4-Benzylamino-phenyl)-1-tert-butylcarbamoyl-ethyl]-2-(3-methyl-butylamino)-3-pyridin-4-yl-propionamide;
N-[2-(4-Benzylamino-phenyl)-1-tert-butylcarbamoyl-ethyl]-2-[methyl-(3-methyl-butyl)-amino]-3-pyridin-4-yl-propionamide;
N-[1-tert-Butylcarbamoyl-2-(4-phenethyl-phenyl)-ethyl]-2-(3-methyl-butylamino)-3-pyridin-4-yl-propionamide;

N-[1-tert-Butylcarbamoyl-2-(4-phenethyl-phenyl)-ethyl]-2-[methyl-(3-methyl-butyl)-amino]-3-pyridin-4-yl-propionamide;

N-[2-(4-Benzyloxy-phenyl)-1-(2-piperidin-1-yl-ethylcarbamoyl)-ethyl]-2-[methyl-(3-methyl-butyl)-amino]-3-pyridin-4-yl-propionamide;

N-[1-(4-Benzyloxy-benzyl)-2-oxo-2-piperidin-1-yl-ethyl]-2-[methyl-(3-methyl-butyl)-amino]-3-pyridin-4-yl-propionamide;

N-[2-(4-Benzyloxy-phenyl)-1-(2-piperidin-1-yl-ethylcarbamoyl)-ethyl]-2-(3-methyl-butylamino)-3-pyridin-4-yl-propionamide;

N-[1-(4-Benzyloxy-benzyl)-2-oxo-2-piperidin-1-yl-ethyl]-2-(3-methyl-butylamino)-3-pyridin-4-yl-propionamide;

N-[2-(4-Benzyloxy-phenyl)-1-tert-butylcarbamoyl-ethyl]-2-(cyclohexyl-methyl-amino)-3-pyridin-3-yl-propionamide;

N-[2-(4-Benzyloxy-phenyl)-1-tert-butylcarbamoyl-ethyl]-2-[methyl-(3-methyl-butyl)-amino]-3-pyridin-3-yl-propionamide;

N-[2-(4-Benzyloxy-phenyl)-1-tert-butylcarbamoyl-ethyl]-2-(isobutyl-methyl-amino)-3-pyridin-3-yl-propionamide;

N-[2-(4-Benzyloxy-phenyl)-1-tert-butylcarbamoyl-ethyl]-2-[(3,3-dimethyl-butyl)-methyl-amino]-3-pyridin-3-yl-propionamide;

N-[2-(4-Benzyloxy-phenyl)-1-tert-butylcarbamoyl-ethyl]-2-(cyclohex-2-enyl-methyl-amino)-3-pyridin-3-yl-propionamide;

N-[2-(4-Benzyloxy-phenyl)-1-tert-butylcarbamoyl-ethyl]-2-[(4-dimethylamino-benzyl)-methyl-amino]-3-pyridin-3-yl-propionamide;

N-[2-(4-Benzyloxy-phenyl)-1-tert-butylcarbamoyl-ethyl]-2-[(4-methoxy-benzyl)-methyl-amino]-3-pyridin-3-yl-propionamide;

N-{1-tert-Butylcarbamoyl-2-[4-(3,3-dimethyl-butyl)-phenyl]-ethyl}-2-[methyl-(3-methyl-butyl)-amino]-3-pyridin-3-yl-propionamide;

N-{1-tert-Butylcarbamoyl-2-[4-(pyridin-2-ylmethoxy)-phenyl]-ethyl}-2-[methyl-(3-methyl-butyl)-amino]-3-pyridin-3-yl-propionamide;

N-{1-tert-Butylcarbamoyl-2-[4-(pyridin-3-ylmethoxy)-phenyl]-ethyl}-2-[methyl-(3-methyl-butyl)-amino]-3-pyridin-3-yl-propionamide;

N-[2-(4-Benzylamino-phenyl)-1-tert-butylcarbamoyl-ethyl]-2-[methyl-(3-methyl-butyl)-amino]-3-pyridin-3-yl-propionamide;

N-[1-tert-Butylcarbamoyl-2-(4-phenethyl-phenyl)-ethyl]-2-[methyl-(3-methyl-butyl)-amino]-3-pyridin-3-yl-propionamide;

N-{1-tert-Butylcarbamoyl-2-[4-(3,3-dimethyl-butyl)-phenyl]-ethyl}-2-(3-methyl-butylamino)-3-pyridin-3-yl-propionamide;

N-{1-tert-Butylcarbamoyl-2-[4-(pyridin-2-ylmethoxy)-phenyl]-ethyl}-2-(3-methyl-butylamino)-3-pyridin-3-yl-propionamide;

N-{1-tert-Butylcarbamoyl-2-[4-(pyridin-3-ylmethoxy)-phenyl]-ethyl}-2-(3-methyl-butylamino)-3-pyridin-3-yl-propionamide;

N-[2-(4-Benzylamino-phenyl)-1-tert-butylcarbamoyl-ethyl]-2-(3-methyl-butylamino)-3-pyridin-3-yl-propionamide;

N-[1-tert-Butylcarbamoyl-2-(4-phenethyl-phenyl)-ethyl]-2-(3-methyl-butylamino)-3-pyridin-3-yl-propionamide;

N-[2-(4-Benzyloxy-phenyl)-1-(2-piperidin-1-yl-ethylcarbamoyl)-ethyl]-2-[(3-methyl-butyl)-amino]-3-pyridin-3-yl-propionamide;

N-[2-(4-Benzyloxy-phenyl)-1-(2-piperidin-1-yl-ethylcarbamoyl)-ethyl]-2-[methyl-(3-methyl-butyl)-amino]-3-pyridin-3-yl-propionamide;

N-[1-(4-Benzyloxy-benzyl)-2-oxo-2-piperidin-1-yl-ethyl]-2-[(3-methyl-butyl)-amino]-3-pyridin-3-yl-propionamide;

N-[1-(4-Benzyloxy-benzyl)-2-oxo-2-piperidin-1-yl-ethyl]-2-[methyl-(3-methyl-butyl)-amino]-3-pyridin-3-yl-propionamide;

N-[2-(4-Benzyloxy-phenyl)-1-tert-butylcarbamoyl-ethyl]-2-(cyclohexyl-methyl-amino)-3-thiazol-4-yl-propionamide;

N-[2-(4-Benzyloxy-phenyl)-1-tert-butylcarbamoyl-ethyl]-2-[methyl-(3-methyl-butyl)-amino]-3-thiazol-4-yl-propionamide;

N-[2-(4-Benzyloxy-phenyl)-1-tert-butylcarbamoyl-ethyl]-2-(isobutyl-methyl-amino)-3-thiazol-4-yl-propionamide;

N-[2-(4-Benzyloxy-phenyl)-1-tert-butylcarbamoyl-ethyl]-2-[(3,3-dimethyl-butyl)-methyl-amino]-3-thiazol-4-yl-propionamide;

N-[2-(4-Benzyloxy-phenyl)-1-tert-butylcarbamoyl-ethyl]-2-(cyclohex-2-enyl-methyl-amino)-3-thiazol-4-yl-propionamide;

N-[2-(4-Benzyloxy-phenyl)-1-tert-butylcarbamoyl-ethyl]-2-[(4-dimethylamino-benzyl)-methyl-amino]-3-thiazol-4-yl-propionamide;

N-[2-(4-Benzyloxy-phenyl)-1-tert-butylcarbamoyl-ethyl]-2-[(4-methoxy-benzyl)-methyl-amino]-3-thiazol-4-yl-propionamide;

N-{1-tert-Butylcarbamoyl-2-[4-(3,3-dimethyl-butyl)-phenyl]-ethyl}-2-[methyl-(3-methyl-butyl)-amino]-3-thiazol-4-yl-propionamide;

N-{1-tert-Butylcarbamoyl-2-[4-(3,3-dimethyl-butyl)-phenyl]-ethyl}-2-[methyl-(3-methyl-butyl)-amino]-3-thiazol-4-yl-propionamide;

N-{1-tert-Butylcarbamoyl-2-[4-(pyridin-2-ylmethoxy)-phenyl]-ethyl}-2-[methyl-(3-methyl-butyl)-amino]-3-thiazol-4-yl-propionamide;

N-{1-tert-Butylcarbamoyl-2-[4-(pyridin-2-ylmethoxy)-phenyl]-ethyl}-2-[methyl-(3-methyl-butyl)-amino]-3-thiazol-4-yl-propionamide;

N-{1-tert-Butylcarbamoyl-2-[4-(pyridin-3-ylmethoxy)-phenyl]-ethyl}-2-[methyl-(3-methyl-butyl)-amino]-3-thiazol-4-yl-propionamide;

N-{1-tert-Butylcarbamoyl-2-[4-(pyridin-3-ylmethoxy)-phenyl]-ethyl}-2-[methyl-(3-methyl-butyl)-amino]-3-thiazol-4-yl-propionamide;

N-[1-tert-Butylcarbamoyl-2-(4-phenethyl-phenyl)-ethyl]-2-[methyl-(3-methyl-butyl)-amino]-3-thiazol-4-yl-propionamide;

N-[1-tert-Butylcarbamoyl-2-(4-phenethyl-phenyl)-ethyl]-2-[methyl-(3-methyl-butyl)-amino]-3-thiazol-4-yl-propionamide;

N-[1-tert-Butylcarbamoyl-2-(4-phenethyl-phenyl)-ethyl]-2-[methyl-(3-methyl-butyl)-amino]-3-thiazol-4-yl-propionamide;

N-[1-tert-Butylcarbamoyl-2-(4-phenethyl-phenyl)-ethyl]-2-[methyl-(3-methyl-butyl)-amino]-3-thiazol-4-yl-propionamide;

N-[2-(4-Benzyloxy-phenyl)-1-(2-piperidin-1-yl-ethylcarbamoyl)-ethyl]-2-(3-methyl-butylamino)-3-thiazol-4-yl-propionamide;

N-[2-(4-Benzyloxy-phenyl)-1-(2-piperidin-1-yl-ethylcarbamoyl)-ethyl]-2-[methyl-(3-methyl-butyl)-amino]-3-thiazol-4-yl-propionamide;

N-[1-(4-Benzyloxy-benzyl)-2-oxo-2-piperidin-1-yl-ethyl]-2-(3-methyl-butylamino)-3-thiazol-4-yl-propionamide; or N-[1-(4-Benzyloxy-benzyl)-2-oxo-2-piperidin-1-yl-ethyl]-2-[methyl-(3-methyl-butyl)-amino]-3-thiazol-4-yl-propionamide.

Also provided is a pharmaceutical composition comprising a compound of Formula I.

Also provided is a method of blocking calcium channels, the method comprising administering to a patient in need of calcium channel blocking a therapeutically effective amount of a compound of Formula I to block calcium channels.

In a preferred embodiment of the method, the calcium channels are N-type calcium channels.

In another embodiment, the present invention provides a method of blocking N-type calcium channels, the method comprising administering to a patient in need of N-type calcium channel blocking a therapeutically effective amount of a compound of Formula I effective to block N-type calcium channels.

The invention also provides a method of treating stroke, the method comprising administering to a patient having or having had a stroke a therapeutically effective amount of a compound of Formula I.

The invention also provides a method of preventing a stroke, the method comprising administering to a patient at risk of having a stroke a therapeutically effective amount of a compound of Formula I.

The invention also provides a method of treating cerebral ischemia, the method comprising administering to a patient having cerebral ischemia a therapeutically effective amount of a compound of Formula I.

The invention also provides a method of treating head trauma, the method comprising administering to a patient having head trauma a therapeutically effective amount of a compound of Formula I.

The invention also provides a method of treating asthma, the method comprising administering to a patient having asthma a therapeutically effective amount of a compound of Formula I.

The invention also provides a method of treating amyotropic lateral sclerosis, the method comprising administering to a patient having treating amyotropic lateral sclerosis a therapeutically effective amount of a compound of Formula I.

Also provided is a method of treating epilepsy, the method comprising administering to a patient having epilepsy a therapeutically effective amount of a compound of Formula I.

Also provided is a method of treating pain, the method comprising administering to a patient having pain a therapeutically effective amount of a compound Formula I.

DETAILED DESCRIPTION OF THE INVENTION

The present invention provides compounds having the Formula I

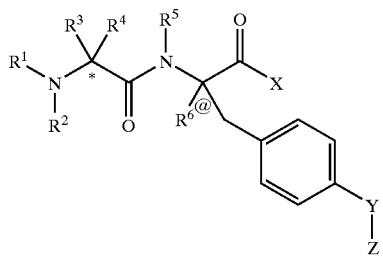

wherein
* denotes a first chiral center when $R^3$ and $R^4$ are different;
@ denotes a second chiral center;
$R^1$ and $R^2$ are independently hydrogen, $C_1$–$C_8$alkyl, $C_3$–$C_7$cycloalkyl, $C_1$–$C_8$substituted alkyl, $C_1$–$C_6$alkoxy, hydroxy, $C_3$–$C_7$cycloalkenyl, $C_3$–$C_7$substituted cycloalkenyl, $C_3$–$C_7$substituted cycloalkyl, —$(CH_2)_n$-aryl, —$(CH_2)_n$-substituted aryl, $C_2$–$C_8$alkenyl, $C_2$–$C_8$substituted alkenyl, —$(CH_2)_n$-heteroaryl, —$(CH_2)_n$-substituted heteroaryl, —$(CH_2)_n$—$C_3$–$C_7$heterocycloalkyl, —$(CH_2)_n$—$C_3$–$C_7$cycloalkyl, —$(CH_2)_n$-substituted $C_3$–$C_7$heterocycloalkyl, or $R^1$ and $R^2$ may be taken together to form a 5- to 7-membered ring which may contain a heteroatom, provided that $R^1$ and $R^2$ are not both hydrogen;

$R^3$, $R^5$, and $R^6$ are independently hydrogen or $C_1$–$C_8$alkyl;

$R^4$ is —$(CH_2)_n$-heteroaryl or —$(CH_2)_n$-substituted heteroaryl;

Y is —$(CH_2)_n$—, —$O(CH_2)_n$—, —$(CH_2)_nO$—, —$N(R^7)(CH_2)_n$—, —$(CH_2)_nN(R^7)$—$S(CH_2)_n$—, —$(CH_2)_nS$—, —C=C—, or —C≡C—;

$R^7$ is hydrogen, methyl, or ethyl;

Z is aryl, substituted aryl, heteroaryl, substituted heteroaryl, $C_3$–$C_7$cycloalkyl, substituted $C_3$–$C_7$cycloalkyl, $C_1$–$C_8$alkyl, $C_3$–$C_7$heterocycloalkyl, or substituted $C_3$–$C_7$heterocycloalkyl;

X is $OR^8$, $NHR^8$, or $NR^8R^9$;

$R^8$ and $R^9$ are independently $C_1$–$C_{12}$alkyl, $C_1$–$C_{12}$substituted alkyl, —$(CH_2)_n$—$C_3$–$C_8$heterocycloalkyl, $C_3$–$C_7$cycloalkyl, substituted $C_3$–$C_7$cycloalkyl, arylalkyl, substituted arylalkyl, heteroarylalkyl, substituted heteroarylalkyl, or $NR^8R^9$ can together with the nitrogen atom form a ring having from 4 to 7 atoms;

each n is 0 to 5, and the pharmaceutically acceptable salts, esters, amides, and prodrugs thereof.

Two chiral centers that can have either R or S configurations are designated above in Formula I by the symbols "*" and "@." It is intended that the present invention cover compounds having the S,S; R,R; S,R; or R,S configurations and mixtures thereof.

The term "alkyl" means a straight or branched chain hydrocarbon. Representative examples of alkyl groups are methyl, ethyl, propyl, isopropyl, isobutyl, butyl, tert-butyl, sec-butyl, pentyl, and hexyl.

The term "alkoxy" means an alkyl group attached to an oxygen atom. Representative examples of alkoxy groups include methoxy, ethoxy, tert-butoxy, propoxy, and isobutoxy.

The term "halogen" includes chlorine, fluorine, bromine, and iodine.

The term "alkenyl" means a branched or straight chain hydrocarbon having one or more carbon-carbon double bond.

The term "aryl" means an aromatic hydrocarbon. Representative examples of aryl groups include phenyl and naphthyl.

The term "heteroatom" includes oxygen, nitrogen, and sulfur.

The term "heteroaryl" means an aryl group wherein one or more carbon atom of the aromatic hydrocarbon has been replaced with a heteroatom. Examples of heteroaryl radicals include, but are not limited to, pyridyl, imidazolyl, pyrrolyl, thienyl, furyl, pyranyl, pyrimidinyl, pyridazinyl, indolyl, quinolyl, naphthyridinyl, and isoxazolyl.

The term "cycloalkyl" means a cyclic hydrocarbon. Examples of cycloalkyl groups include cyclopropyl, cyclobutyl, cyclopentyl, and cyclohexyl.

The symbol "—" means a bond.

The term "patient" means all animals including humans. Examples of patients include humans, cows, dogs, cats, goats, sheep, and pigs.

The term "substituted" means that the base organic radical has one or more substituents. For example, substituted cyclohexyl means a cyclohexyl radical that has one or more substituents. Substituents include, but are not limited to, halogen, $C_1$–$C_8$alkyl, —CN, $CF_3$, —$NO_2$, —$NH_2$, —$NHC_1$–$C_8$alkyl, —N ($C_1$–$C_8$alkyl)$_2$, —OC 1–$C_8$alkyl, and —OH. Particularly preferred substituents include, but are not limited to, tert-butyl, methyl, chlorine, fluorine, bromine, —$OCH_3$, —$OCH_2CH_3$, —OH, and —$N(CH_3)_2$.

The term "cycloalkenyl" means a cycloalkyl group having at least one carbon-carbon double bond. Examples of cycloalkenyl groups include cyclopentene, cyclobutene, and cyclohexene.

The term "heterocycloalkyl" means a cycloalkyl group wherein one or more carbon atom is replaced with a heteroatom. Examples of heterocycloalkyl groups include, but are not limited to, pyrrolidinyl, piperidinyl, and piperazinyl.

Those skilled in the art are easily able to identify patients having or having had a stroke or at risk of having a stroke, cerebral ischemia, head trauma, asthma, amyotropic lateral sclerosis, or epilepsy. For example, patients who are at risk of having a stroke include, but is not limited to, patients having hypertension or undergoing major surgery.

A therapeutically effective amount is an amount of a compound of Formula I, that when administered to a patient, ameliorates a symptom of the disease.

The compounds of the present invention can be administered to a patient either alone or a part of a pharmaceutical composition. The compositions can be administered to patients either orally, rectally, parenterally (intravenously, intramuscularly, or subcutaneously), intracisternally, intravaginally, intraperitoneally, intravesically, locally (powders, ointments, or drops), or as a buccal or nasal spray.

Compositions suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragées, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate and laurylsulphonate salts, and the like. These may include cations based on the alkali and alkaline earth metals, such as sodium, lithium, potassium, calcium, magnesium, and the like, as well as non-toxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M. et al., "Pharmaceutical Salts," *J. Pharm. Sci.*, 1977;66:1–19 which is incorporated herein by reference.)

Examples of pharmaceutically acceptable, non-toxic esters of the compounds of this invention include $C_1$–$C_6$alkyl esters wherein the alkyl group is a straight or branched chain. Acceptable esters also include $C_5$–$C_7$cycloalkyl esters as well as arylalkyl esters such as, but not limited to, benzyl. $C_1$–$C_4$alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$alkyl amines and secondary $C_1$–$C_6$dialkyl amines wherein the alkyl groups are straight or branched chain. In the case of secondary amines, the amine may also be in the form of a 5- or 6-membered heterocycloalkyl group containing one nitrogen atom. Amides derived from ammonia, $C_1$–$C_3$alkyl primary amines, and $C_1$–$C_2$dialkyl secondary amines are preferred. Amides of the compounds of the invention may be prepared according to conventional methods.

The term "prodrug" refers to compounds that are rapidly transformed in vivo to yield the parent compound of the above formula, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are incorporated herein by reference.

In addition, the compounds of the present invention can exist in unsolvated, as well as solvated forms, with pharmaceutically acceptable solvents such as water, ethanol, and the like. In general, the solvated forms are considered equivalent to the unsolvated forms for the purposes of the present invention.

The compounds of the present invention can exist in different stereoisomeric forms by virtue of the presence of asymmetric centers in the compounds. It is contemplated that all stereoisomeric forms of the compounds, as well as mixtures thereof including racemic mixtures, form part of this invention.

The compounds of the present invention can be administered to a patient at dosage levels in the range of about 0.1 to about 1,000 mg per day. For a normal human adult having a body weight of about 70 kilograms, a dosage in the range of about 0.01 to about 100 mg per kilogram of body weight per day is preferable. The specific dosage used, however, can vary. For example, the dosage can depend on a numbers of factors including the requirements of the patient, the severity of the condition being treated, and the pharmacological activity of the compound being used. The determination of optimum dosages for a particular patient is well-known to those skilled in the art.

In addition, it is intended that the present invention cover compounds made either using standard organic synthetic techniques, including combinatorial chemistry or by biological methods, such as through metabolism.

The examples presented below are intended to illustrate particular embodiments of the invention and are not intended to limit the scope of the specification, including the claims, in any way.

The following abbreviations are used throughout this application:

| | |
|---|---|
| Pr | propyl |
| Et | ethyl |
| HBTU | 2-(1H-benzotriazol-1yl)-1,1,3,3-tetramethyl uranium hexafluorophosphate |
| Bz or Bn | benzyl |
| TFA | trifluoroacetic acid |
| APCI | atmospheric pressure chemical ionization |
| NMR | nuclear magnetic resonance |
| TLC | thin layer chromatography |
| HPLC | high pressure liquid chromatography |
| DMF | dimethyl formamide |
| EtOAC | ethyl acetate |
| EtOH | ethanol |
| MS | mass spectrum |
| DCM | dichloromethane |
| $Et_3N$ | triethyl amine |
| THF | tetrahydrofuran |
| IR | infrared |
| Oac | acetate |
| bu | butyl |
| iso-pr | iso-propyl |
| FMOC | 9-fluorenylmethyloxycarbonyl |
| BOC | tertiary butyloxycarbonyl |

EXAMPLES

General Procedure for the Preparation of Peptidylamines (IV)

Scheme 1

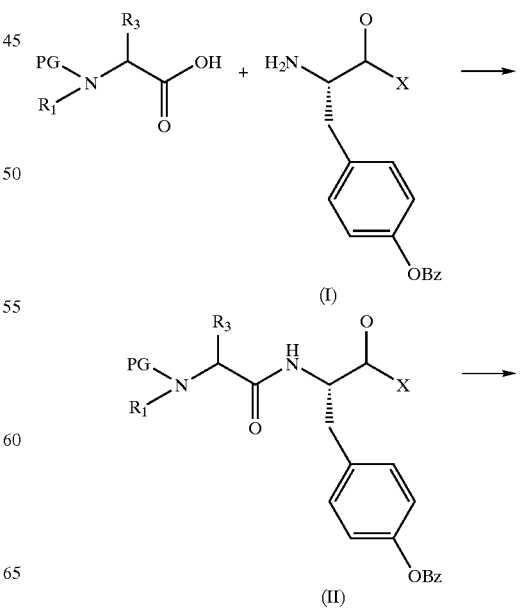

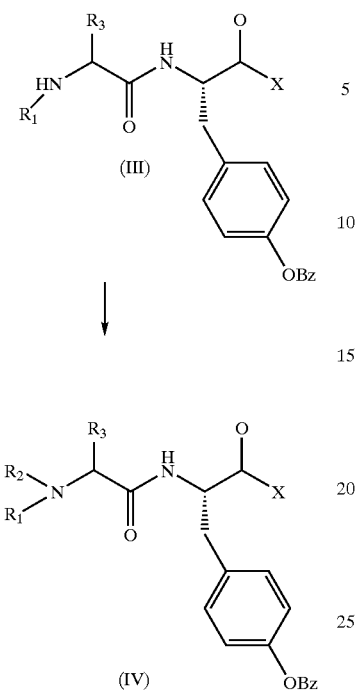
PG = Protecting group
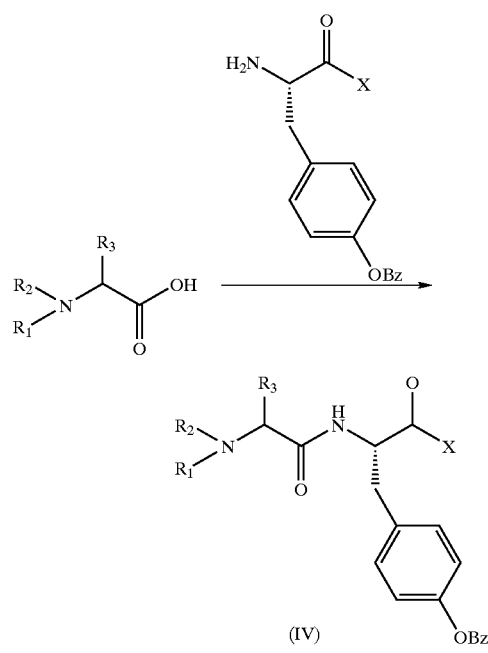
Example 1
[S—(R*,R*)]—N-[2-(4-Benzyloxy-phenyl)-1-tert-butylcarbamoyl-ethyl]-2-(3-methyl-butylamino)-3-pyridin-4-yl-propionamide
Scheme 2
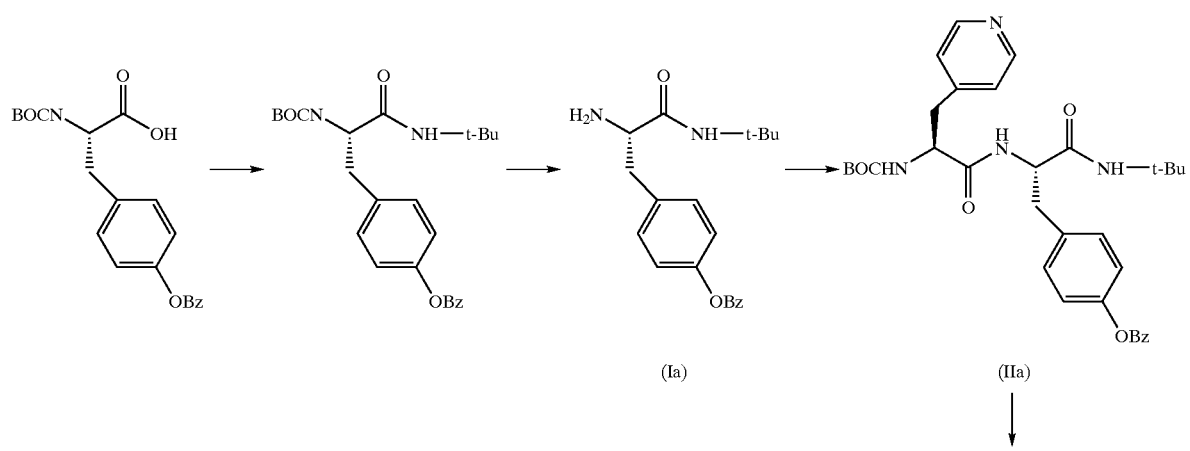

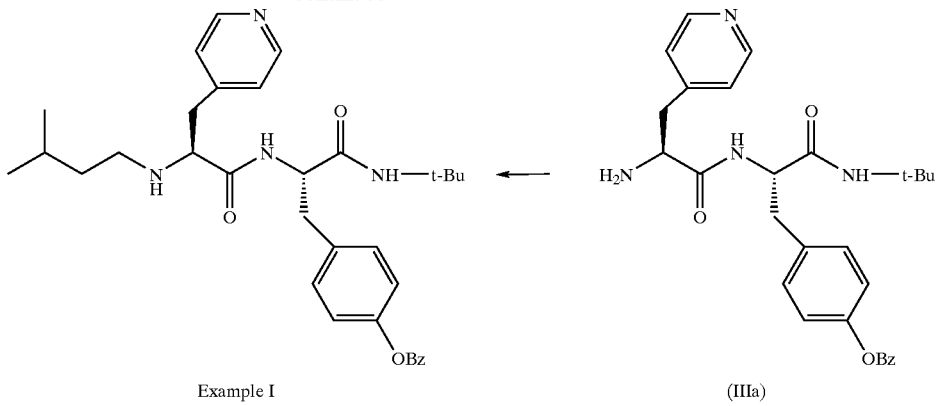

Example I            (IIIa)

Step 1: The preparation of (S)-[2-(4-Benzyloxy-phenyl)-1-tert-butylcarbamoyl-ethyl]-carbamic acid tert-butyl ester N-Boc-O-Benzyl-tyrosine (20.0 g, 53.9 mmol) was dissolved in DMF (270 mL) and treated with diisopropylethylamine (19 mL, 108 mmol), tert-butylamine (5.7 mL. 53.9 mmol), and HBTU (13.9 g, 53.9 mmol). The reaction was stirred for 15 minutes and then diluted with EtOAc (1 L), washed with saturated bicarbonate solution (2×1 L) and brine (1 L), dried over $Na_2SO_4$ and concentrated to give 22.1 g (92%) of(S)-[2-(4-Benzyloxy-phenyl)-1-tert-butylcarbamoyl-ethyl]-carbamic acid tert-butyl ester.

MS: 428 (M+1 for $C_{25}H_{34}N_2O_4$);
TLC: $SiO_2$, $R_f$ 0.49 (10% $MeOH/CH_2Cl_2$).

Step 2: The preparation of (S)-2-Amino-3-(4-benzyloxy-phenyl)-N-tert-butyl-propionamide (Ia)

(S)-[2-(4-Benzyloxy-phenyl)-1-tert-butylcarbamoyl-ethyl]-carbamic acid tert-butyl ester (6.0 g, 14.1 mmol) was dissolved in $CH_2Cl_2$ (28 mL) and treated with trifluoroacetic acid (28 mL). The reaction was stirred for 20 minutes and then concentrated. The residue was diluted with EtOAc (300 mL), washed with saturated bicarbonate solution (2×300 mL) and brine (300 mL), dried over $Na_2SO_4$, and concentrated to give 4.2 g (91%) of Ia.

MS: 328 (M+1 for $C_{20}H_{26}N_2O_3$);
TLC: $SiO_2$, $R_f$ 0.43 (10% $MeOH/CH_2Cl_2$).

Step 3: The preparation of [S—(R*,R*)]-{1-[2-(4-Benzyloxy-phenyl)-1-tert-butylcarbamoyl-ethylcarbamoyl]-2-pyridin-4-yl-ethyl}-carbamic acid tert-butyl ester (IIa)

(S)-2-Amino-3-(4-benzyloxy-phenyl)-N-tert-butyl-propionamide (1.49 g, 4.56 mmol) (Ia) was dissolved in DMF (23 mL) and treated with diisopropylethylamine (2.4 mL, 13.7 mmol), N-Boc-L-4-pyridylalanine (1.21 g, 4.56 mmol), and HBTU (1.73 g, 4.56 mmol). The reaction was stirred for 2 hours and then diluted with EtOAc (200 mL), washed with saturated bicarbonate solution and brine, dried over $Na_2SO_4$, and concentrated. The crude material was chromatographed on silica gel eluting with 8% MeOH to give 2.51 g (96%) of (IIa).

MS: 575 (M+1 for $C_{33}H_{42}N_4O_5$);
TLC: $SiO_2$, $R_f$ 0.21 (6% $MeOH/CH_2Cl_2$).

Step 4: The preparation of [S—(R*,R*)]-2-Amino-N-[2-(4-benzyloxy-phenyl)-1-tert-butylcarbamoyl-ethyl]-3-pyridin-4-yl-propionamide (IIIa)

[S—(R*,R*)]-{1-[2-(4-Benzyloxy-phenyl)-1-tert-butylcarbamoyl-ethylcarbamoyl]-2-pyridin-4-yl-ethyl}-carbamic acid tert-butyl ester (IIa) (2.48 g, 4.31 mmol) was dissolved in $CH_2Cl_2$ (15 mL) and treated with TFA. The reaction was stirred for 30 minutes, then concentrated in vacuo, diluted with EtOAc (400 mL), washed with saturated bicarbonate (2×400 mL) and brine (1×400 mL), dried over $Na_2SO_4$, and concentrated in vacuo to give 1.80 g (88%) of (IIIa) as a white foam.

MS: 475 (M+1 for $C_{28}H_{34}N_4O_3$);
TLC: $SiO_2$, $R_f$ 0.33 (10% $MeOH/CH_2Cl_2$).
Analysis calculated for $C_{28}H_{34}N_4O_3$ 0.75$H_2O$): C, 68.90; H, 7.33; N, 11.48.
Found: C, 68.57; H, 6.94; N, 11.17.

Step 5: Example 1, [S—(R*,R*)]—N-[2-(4-Benzyloxy-phenyl)-1-tert-butylcarbamoyl-ethyl]-2-(3-methyl-butylamino)-3-pyridin-4-yl-propionamide

[S—(R*,R*)]-2-Amino-N-[2-(4-benzyloxy-phenyl)-1-tert-butylcarbamoyl-ethyl]-3-pyridin-4-yl-propionamide (IIIa) (0.2 g, 0.42 mmol) was dissolved in $CH_2Cl_2$ (4 mL) and treated with isovaleraldehyde (45 μL, 0.42 mmol) and stirred for 30 minutes. The reaction was cooled to 0° C. in an ice bath, treated with $NaBH(OAc)_3$ (0.134 g, 0.63 mmol), then allowed to come to room temperature as the ice melted and stir overnight. The reaction was diluted with EtOAc (100 mL), washed with saturated bicarbonate solution and brine, dried over $Na_2SO_4$, and concentrated. The residue was chromatographed on silica gel eluting with 6% MeOH/$CH_2Cl_2$ to give 0.167 g (73%) of Example 1.

MS: 545 (M+1 for $C_{33}H_{44}N_4O_3$);
sticky solid;
TLC: $R_f$ 0.3 (6% $MeOH/CH_2Cl_2$).
Analysis calculated for $C_{33}H_{44}N_4O_3$.0.75$H_2O$: C, 71.00; H, 8.22; N, 10.04.
Found: C, 71.00; H, 8.11; N, 10.35.

Example 2
[S-(R*,R*)]—N-[2-(4-Benzyloxy-phenyl)-1-tert-butylcarbamoyl-ethyl]-2-(cyclohex-2-enylamino)-3-pyridin-4-yl-propionamide A mixture of IIIa (0.237 g, 0.5 mmol), diisopropylethylamine (0.39 mg, 3 mmol), 3-bromocyclohexene (0.08 g, 0.5 mmol), and anhydrous THF (30 mL) was stirred at 40° C. for 18 hours. The precipitate was filtered off. The reaction mixture was concentrated and purified by column chromatography on silica gel eluting with EtOAc to give the titled compound (70 mg, 25% yield). The title compound was further converted to its HCl salt by HCl/ether treatment.

MS: 555 (M+1 for $C_{34}H_{42}N_4O_3$);
mp 163–164° C.;
TLC: $R_f$ 0.1 (EtOAc) for the free base.
Analysis calculated for $C_{34}H_{42}N_4O_3$.2 HCl.2$H_2O$: C, 61.53; H, 6.98; N: 8.44.
Found: C, 61.12; H, 7.21; N, 7.98.

Example 3
[S-(R*,R*)]—N-[2-(4-Benzyloxy-phenyl)-1-tert-butylcarbamoyl-ethyl]-2-(3-methyl-butylamino)-3-pyridin-3-yl-propionamide

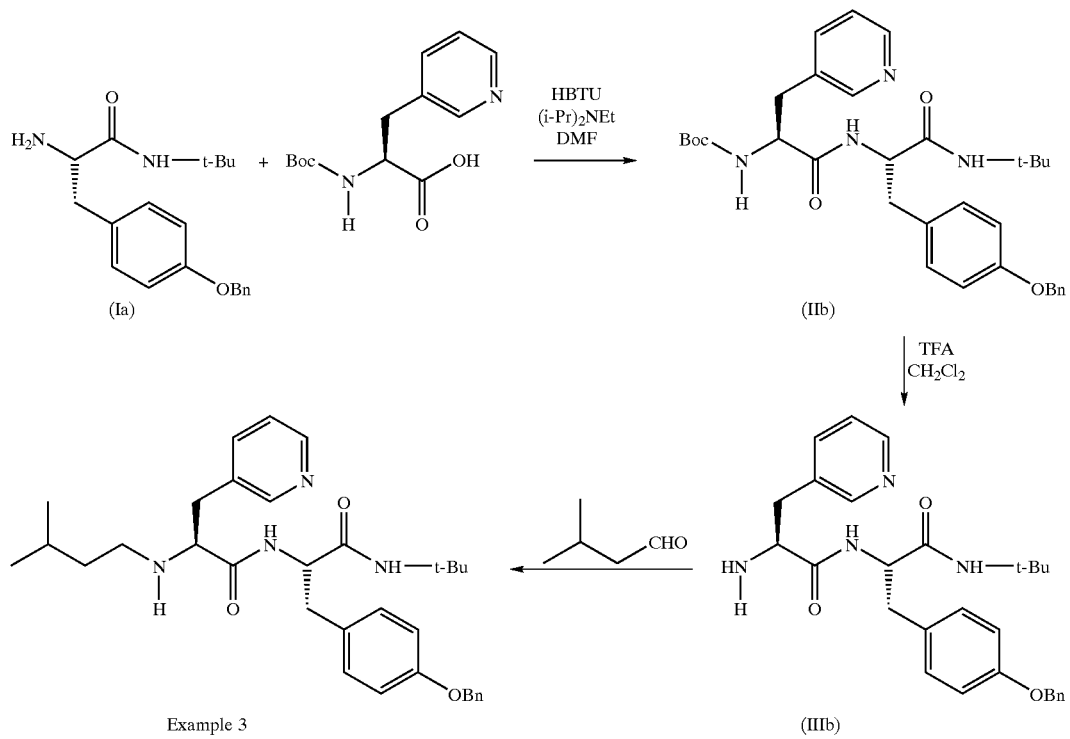

Step 1: The Preparation of [S-(R*,R*)]-2-Amino-N-[2-(4-benzyloxy-phenyl)-1-tert-butylcarbamoyl-ethyl]-3-pyridin-3-yl-propionamide (IIIb)

(S)-2-Amino-3-(4-benzyloxy-phenyl)-N-tert-butyl-propionamide (0.48 g, 1.5 mmol) (Ia) was dissolved in $CH_3CN$ (80 mL) and treated with diisopropylethylamine (0.3 g, 2.2 mmol), N-BOC-3-pyridylalanine (0.4 g, 1.5 mmol), and HBTU (0.57 g, 1.5 mmol). The reaction was stirred for 15 hours and then concentrated. The residue was dissolved in EtOAc (200 mL), washed with saturated bicarbonate solution (2×100 mL) and brine (100 mL), dried over $Na_2SO_4$, and concentrated. The crude material was further dissolved in $CH_2Cl_2$ (8 mL), then TFA (8 mL) was added, and it was stirred for 30 minutes and concentrated to dryness. The crude product was dissolved in $CH_2Cl_2$ (50 mL), washed with $NaHCO_3$ (aq.), dried over $NaHCO_3$ (powder), and concentrated to yield IIIb (0.73 g). IIIb was further converted to its HCl salt by HCl/ether treatment to yield 0.75 g of salt.

MS: 474 (M+ for $C_{28}H_{34}N_4O_3$);
mp 180–181° C.;
TLC: $SiO_2$, $R_f$ 0.2 (10% MeOH/EtOAc) for the free base.
Analysis calculated for $C_{28}H_{34}N_4O_3 \cdot 2HCl \cdot 1.75H_2O$: C, 58.08; H, 6.89; N, 9.68.
Found: C, 58.27; H, 6.83; N, 9.47.

Step 2: Example 3 [S—(R*,R*)]—N-[2-(4-Benzyloxy-phenyl)-1-tert-butylcarbamoyl-ethyl]-2-(3-methyl-butylamino)-3-pyridin-3-yl-propionamide (IIIbz)

Two HCl (0.15 g, 0.27 mmol) was dissolved in $CH_2Cl_2$ (20 mL) and treated with isovaleraldehyde (0.024 mL, 0.27 mmol). The reaction was stirred for 30 minutes, then cooled to 0° C. and treated with sodium triacetoxyborohydride (0.084 g, 0.4 mmol). The reaction was allowed to warm to room temperature and stir overnight. The reaction was diluted with $CH_2Cl_2$ (60 mL), washed with saturated bicarbonate solution (2×60 mL) and brine (60 mL), dried over $Na_2SO_4$, and concentrated. The residue was chromatographed on silica gel eluting with 10% MeOH/$CH_2Cl_2$ to give 0.08 g (50%) of the title compound. Example 3 was further converted to its HCl salt by HCl/ether treatment to yield the HCl salt (0.08 g).

MS: 545 (M+ for $C_{33}H_{45}N_4O_3$);
mp 166–167° C.;
TLC: $SiO_2$, $R_f$ 0.1 (10% MeOH/$CH_2Cl_2$) for the free base.
Analysis calculated for $C_{33}H_{45}N_4O_3 \cdot 2HCl \cdot 2.25H_2O$: C, 60.13; H, 7.72; N, 8.50.
Found: C, 60.51; H, 7.73; N, 7.96.

Example 4
[S—(R*,R*)]—N-[2-(4-Benzyloxy-phenyl)-1-tert-butylcarbamoyl-ethyl]-2-(cyclohex-2-enylamino)-3-pyridin-3-yl-propionamide A mixture of IIIb (0.237 g, 0.5 mmol), diisopropylethylamine (0.39 g, 3 mmol), 3-bromocyclohexene (0.08 g, 0.5 mmol), and anhydrous THF (30 mL) was stirred at 40° C. for 18 hours. The precipitate was filtered off. The reaction mixture was concentrated and purified by column chromatography on silica gel eluting with EtOAc to give the title compound (70 mg, 25% yield). The title compound was further converted to its HCl salt by HCl/ether treatment to yield 70 mg of the product.

MS: 555 (M+1 for $C_{34}H_{42}N_4O_3$);
mp 185–186° C.;
TLC: $R_f$ 0.1 (EtOAc) for the free base.
Analysis calculated for $C_{34}H_{42}N_4O_3 \cdot 2HCl \cdot 1.5H_2O$: C, 62.37; H, 7.23; N, 8.56.
Found: C, 62.41; H, 7.18; N, 8.24.

Example 5
[S—(R*,R*)]—N-[2-(4-Benzyloxy-phenyl)-1-tert-butylcarbamoyl-ethyl]-2-(3-methyl-butylamino)-3-thiazol-4-yl-propionamide

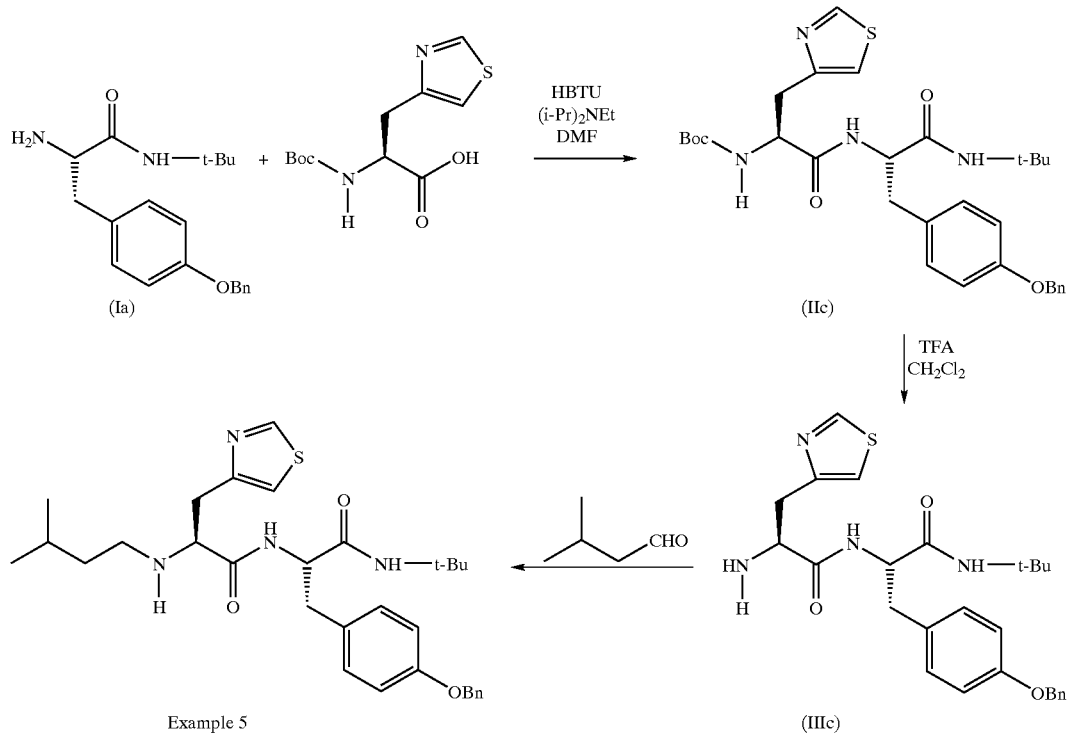

Step 1: The preparation of [S—(R*,R*)]-{1[-2-(4-Benzyloxy-phenyl)-1-tert-butylcarbamoyl-ethylcarbamoyl]-3-thiazol-4-yl-ethyl}-carbamic acid tert-butyl ester) (IIc)

(S)-2-Amino-3-(4-benzyloxy-phenyl)-N-tert-butyl-propionamide (0.408 g, 1.5 mmol) (Ia) was dissolved in $CH_3CN$ (80 mL) and treated with diisopropylethylamine (0.3 g, 2.2 mmol), N-Boc-4-thiazoyalanine (0.49 g, 1.5 mmol), and HBTU (0.57 g, 1.5 mmol). The reaction was stirred for 30 minutes and then concentrated. The residue was dissolved in EtOAc (60 mL), washed with saturated bicarbonate solution (2×100 mL), dried over $Na_2SO_4$, and concentrated. The crude material was chromatographed on silica gel eluting with EtOAc to give 0.8 g (92%) of (IIc).

MS: 582 (M+ for $C_{31}H_{41}N_4O_5S_1$);
TLC: $SiO_2$, TLC: $R_f 0.8$ (EtOAc);
mp 140–141° C.

Analysis calculated for $C_{31}H_{41}N_4O_5S_1$: C, 64.00; H, 7.10; N, 9.63.

Found: C, 63.77; H, 6.94; N, 9.49.

Step 2: The preparation of [S—(R*,R*)]-2-Amino-N-[2-(4-benzyloxy-phenyl)-1-tert-butylcarbamoyl-ethyl]-3-thiazol-4-yl-propionamide (IIIc)

A reaction mixture of IIc (0.8 g, 1.37 mmol) in $CH_2Cl_2$ (15 mL) was added TFA (15 mL), stirred for 30 minutes, and concentrated to dryness. The crude product was dissolved in $CH_2Cl_2$ (30 mL), washed with $NaHCO_3$ (aq.), dried over $NaHCO_3$ (powder), concentrated, and purified by column chromatography ($SiO_2$, 50% hexanes/EtOAc) to yield IIIc (0.5 g). IIIc (0.25 g) was further converted to its HCl salt by HCl/ether treatment to yield 0.1 g of the salt.

MS: 481 (M+ for $C_{26}H_{33}N_4O_3S_1$);
TLC: $SiO_2$, TLC: $R_f 0.1$ (10% MeOH/EtOAc) for the free base;
mp 170–171° C.

Analysis calculated for $C_{26}H_{33}N_4O_3S_1.2HCl.1.25H_2O$: C, 54.11; H, 9.70; N, 6.50.

Found: C, 54.39; H, 9.39; N, 6.34.

Step 3: Example 5 [S—(R*,R*)]-N-[2-(4-Benzyloxy-phenyl)-1-tert-butylcarbamoyl-ethyl]-2-(3-methyl-butylamino)-3-thiazol-4-yl-propionamide To a reaction mixture of IIIc free base (0.2 g, 0.41 mmol) in $CH_2Cl_2$ (20 mL) was added isovaleraldehyde (0.036 g, 0.27 mmol) and stirred for 30 minutes at 23° C. Then, the reaction mixture was cooled to 0° C. and treated with sodium triacetoxyborohydride (0.084 g, 0.4 mmol); the reaction was allowed to warm to room temperature and stir overnight. The reaction was diluted with $CH_2Cl_2$ (60 mL), washed with saturated bicarbonate solution (2×60 mL) and brine (60 mL), dried over $Na_2SO_4$, and concentrated. The residue was chromatographed on silica gel eluting with 10% MeOH/EtOAc to give 0.17 g (75% of yield) of the title compound. Example 5 was further converted to its HCl salt by HCl/ether treatment to yield the HCl salt (170 mg).

MS: 551 (M+ for $C_{31}H_{43}N_4O_3S_1$);
mp 236–237° C.;
TLC: $SiO_2$, $R_f 0.7$ (10% MeOH/EtOAc).

Analysis calculated for $C_{31}H_{43}N_4O_3.2HCl$: C, 59.60; H, 7.26; N, 8.92.

Found: C, 60.25; H, 7.44; N, 8.85.

Example 6
[S—(R*,R*)]—N-[2-(4-Benzyloxy-phenyl)-1-tert-butylcarbamoyl-ethyl]-2-(cyclohex-2-enylamino)-3-thiazol-4-yl-propionamide A mixture of IIIc (0.31 g, 0.64 mmol), diisopropylethylamine (0.39 mg, 3 mmol), 3-bromocyclohexene (0.103 g, 0.64 mmol), and anhydrous THF (30 mL) was stirred at 40° C. for 15 hours. The precipitate was filtered off. The reaction mixture was concentrated and purified by column chromatography on silica gel eluting with EtOAc to give the titled compound (150 mg, 45% yield). The title compound was further converted to its HCl salt by HCl/ether treatment.

MS: 561 (M+1 for $C_{32}H_{40}N_4O_3S_1$);
mp 243–244° C.;
TLC: $R_f$ 0.5 (EtOAc) for the free base;
Analysis calculated for $C_{32}H_{40}N_4O_3S_1 \cdot 2HCl$: C, 60.65; H, 6.68; N, 8.84.
Found: C, 60.51; H, 6.99; N, 8.81.

Example 7

[S—(R*,R*)]-N-[2-(4-Benzyloxy-phenyl)-1-tert-butylcarbamoyl-ethyl]-2-cyclohexylamino-3-thiazol-4-yl-propionamide To a reaction mixture of IIIc free base (0.24 g, 0.5 mmol) in $CH_2Cl_2$ (30 mL) was added cyclohexanone (0.05 g, 0.5 mmol) and stirred for 30 minutes at 23° C. Then, the reaction mixture was cooled to 0° C. and treated with sodium triacetoxyborohydride (0.159 g, 0.75 mmol); the reaction was allowed to warm to room temperature and stir overnight. The reaction was diluted with $CH_2Cl_2$ (60 mL), washed with saturated bicarbonate solution (2×60 mL) and brine (60 mL), dried over $Na_2SO_4$, and concentrated. The residue was chromatographed on silica gel eluting with 10% MeOH/EtOAc to give 0.27 g (96% of yield) of the title compound. Example 7 was further converted to its HCl salt by HCl/ether treatment to yield the HCl salt (270 mg).

MS: 563 (M+ for $C_{32}H_{43}N_4O_3S_1$);
mp 160–161° C.;
TLC: $SiO_2$, $R_f$ 0.7 (10% MeOH/EtOAc).
Analysis calculated for $C_{32}H_{43}N_4O_3S_1 \cdot 2HCl \cdot 1.25H_2O$: C, 58.40; H, 7.22; N, 8.51.
Found: C, 58.20; H, 7.46; N, 8.14.

Example 8

[S—(R*,R*)]—N-[2-(4-Benzyloxy-phenyl)-1-tert-butylcarbamoyl-ethyl]-2-(cyclohexylmethyl-amino)-3-(1H-imidazol-4-yl)-propionamide Step 1: The preparation of [S—(R*,R*)]-4-{2-[2-(4-Benzyloxy-phenyl)-1-tert-butylcarbamoyl-ethylcarbamoyl]-2-tert-butoxycarbonylamino-ethyl}-imidazole-1-carboxylic acid tert-butyl ester A solution of 4-(S)-(2-tert-butoxycarbonylamino-2-carboxy-ethyl)-imidazole-1-carboxylic acid tert-butyl ester (1.73 g, 4.0 mmol), 4-methylmorpholine (1.32 mL, 12.0 mmol), HBTU (1.52 g, 4.0 mmol) in 14 mL dry DMF was stirred for 45 minutes, then a solution of (S)-2-amino-3-(4-benzyloxy-phenyl)-N-tert-butyl-propionamide hydrochloride (1.52 g, 4.2 mmol in 10 mL DMF) was added and the resulting solution stirred an additional 30 minutes. The reaction mixture was diluted with 50 mL diethyl ether and washed with 50 mL saturated aqueous sodium bicarbonate solution and twice with 50 mL brine, dried over anhydrous sodium sulfate, and concentrated at reduced pressure. The residue thus obtained was purified by silica gel chromatography using 50% to 80% ethyl acetate in hexanes as eluent, to give 1.97 g (74%) of the title compound.

MS: 663.8 (M+1 for $C_{36}H_{49}N_5O_7$);
mp 81–89° C.

Step 2: The preparation of [S—(R*,R*)]-2-Amino-N-[2-(4-benzyloxy-phenyl)-1-tert-butylcarbamoyl-ethyl]-3-(1H-imidazol-4-yl)-propionamide A solution of [S—(R*,R*)]-4-{2-[2-(4-benzyloxy-phenyl)-1-tert-butylcarbamoyl-ethylcarbamoyl]-2-tert-butoxycarbonylamino-ethyl}-imidazole-1-carboxylic acid tert-butyl ester (1.92 g, 2.87 mmol) in 70 mL dichloromethane was cooled to 3° C., then TFA (14 mL) was added. The resulting solution was warmed to 25° C. and stirred 2 hours. The mixture was concentrated at reduced pressure to a viscous amber oil which was dissolved in 100 mL ethyl acetate and washed twice with 100 mL saturated aqueous sodium bicarbonate solution and twice with 100 mL brine, dried over anhydrous sodium sulfate, and concentrated at reduced pressure affording 1.18 g (85%) of the title compound.

MS: 463.9 (M+1 for $C_{26}H_{33}N_5O_3$);
mp 78–83° C.

Step 3: The preparation of [S—(R*,R*)]—N-[2-(4-Benzyloxy-phenyl)-1-tert-butylcarbamoyl-ethyl]-2-(cyclohexylmethyl-amino)-3-(1H-imidazol-4-yl)-propionamide A solution of [S—(R*,R*)]-2-amino-N-[2-(4-benzyloxy-phenyl)-1-tert-butylcarbamoyl-ethyl]-3-(1H-imidazol-4-yl)-propionamide (350 mg, 0.755 mmol) and cyclohexanecarboxaldehyde (0.091 mL, 0.755 mmol) in 5 mL 1,2-dichloroethane was stirred for 30 minutes. Sodium triacetoxyborohydride (240 mg, 1.13 mmol) was added to the reaction mixture at 3° C., and the mixture was maintained at 3° C. for 30 minutes. Then it was warmed to 25° C. and stirred 16 hours, at which time 35 mL saturated aqueous sodium bicarbonate solution was added and the resulting mixture stirred 30 minutes. Layers were separated, and the aqueous layer extracted with two 25 mL portions of chloroform. The combined organic extracts were dried over anhydrous magnesium sulfate and concentrated at reduced pressure affording 448 mg light tan foam, which was chromatographed on silica gel with 3% methanol in chloroform as eluent to give 125 mg of material, which was further purified by preparative thin layer chromatography on a 1000 micron silica gel plate eluted with 5% methanol in chloroform. The major band was isolated and extracted to give 81 mg (19%) of the title compound, which contained 0.1 mol of trifluoroacetic acid.

MS: 560.0 (M+1 for $C_{33}H_{45}N_5O_3$);
mp: 163–165° C.
Analysis calculated for $C_{33}H_{45}N_5O_3 \cdot 0.1CF_3CO_2H$: C, 69.82; H, 7.96; N, 12.26.
Found: C, 69.49; H, 8.00; N, 11.94.

Example 9

[S—(R*,R*)]N-[2-(4-Benzyloxy-phenyl)-1-tert-butylcarbamoyl-ethyl]-2-(1-methylethyl-amino)-3-(1H-imidazol-4-yl)-propionamide Step 1: The Preparation of 3-(1H-imidazol-4-yl)-2-isopropylamino-propionic acid A mixture of L-histidine (15.51 g, 100 mmol) and acetone (14.7 mL, 200 mmol) was agitated in an atmosphere of hydrogen (pressure, 46–51 psi) at 40° C. in 500 mL ethanol in the presence of Pd/C (20%, 2 g) until the absorption of hydrogen had ceased. The mixture was filtered, and the filtrate was concentrated to dryness under reduced pressure. The white solid thus obtained was triturated with ethanol and dried under vacuum to give 7.31 g (37%) of the title compound as a white solid.

MS (M+ for $C_9H_{15}N_3O_2$)=198.2;
mp 180–188° C. (dec.).

Step 2: The preparation of [S—(R*,R*)]—N-[2-(4-Benzyloxy-phenyl)-1-tert-butylcarbamoyl-ethyl]-3-(1H-imidazol-4-yl)-2-isopropylamino-propionamide A solution of N-isopropylhistidine (302 mg, 1.53 mmol), (S)-2-amino-3-(4-benzyloxy-phenyl)-N-tert-butyl-propionamide (500 mg, 1.32 mmol), and benzyltrimethylammonium methoxide (40% solution in methanol, 2.1 mL, 3.36 mmol) in 10 mL dry DMF was cooled to 3° C. Then, HBTU (581 mg, 1.53 mmol) was added and the resulting mixture stirred at 3° C. for 60 minutes, warmed to 25° C., diluted with 35 mL diethyl ether, and washed with saturated aqueous sodium bicarbonate solution (35 mL) as well as with brine (35 mL), dried over anhydrous sodium sulfate, and concentrated at reduced pressure. The residue thus obtained was further purified twice by silica gel chromatography using 10% methanol in chloroform as eluant, to give 122 mg (13%) of the title compound as the dihydrochloride salt.

MS ($M^+$ for $C_{29}H_{39}N_5O_3$)=506.2;
mp 171–180° C.
Analysis calculated for $C_{29}H_{39}N_5O_3 \cdot 2HCl \cdot 1.25H_2O$: C, 57.95; H, 7.29; N, 11.65.
Found: C, 58.05, H, 7.15, N, 11.44.

Biological Activity

The compounds of the present invention exhibit valuable biological properties because of their ability to block calcium flux through N-type voltage-gated calcium channels. To measure interaction at the N-type $Ca^{2+}$ channel and calcium flux inhibition, the effects of the compounds of the present invention were measured in the assays described below.

Measurement of N-type $Ca^{2+}$ Channel Blocking Potencies of Compounds in IMR-32 Cells Using the Fluorescent $Ca^{2+}$ Indicator Indo-1

IMR-32 cells are a human tumoral cell line of neural origin. The IMR-32 cell line has been shown to contain both N- and L-type voltage sensitive calcium channels. Calcium flux into these cells may be induced by stimulation with elevated potassium concentrations. The L-channel component of calcium flux may be blocked by adding 5 $\mu$M nitrendipine. The remaining component of calcium entry into the IMR-32 cells is due to calcium flux through N-type calcium channels. Intracellular calcium concentrations are measured using the fluorescent calcium indicator Indo-1. The effect of drug concentration on calcium uptake is studied.

Methods

The IMR-32 cell line was obtained from the American Type Culture Collection (Rockville, Md.). Cells were grown in Eagle's Minimum Essential Medium with Earle's salts supplemented with 10% fetal bovine serum, 2 mM L-Gln and antibiotic/antimycotic mixture (Gibco). At approximately 80% confluency, differentiation was induced by the addition of 1 mM dibutyryl cAMP and 2.5 $\mu$M bromodeoxyuridine to the medium. After 7 to 13 days of differentiation, cells were detached using 0.5 mM EDTA and loaded with 5 $\mu$M Indo-1 acetoxymethyl ester (Molecular Probes, Eugene, Oreg.) at 30° C. for 45 minutes Loaded cells were washed twice, resuspended (~$10^7$ cells/mL) in assay buffer (10 mM HEPES/Tris pH 7.4 in Hank's Balanced Salt Solution without bicarbonate or phenol red containing 0.5% bovine serum albumin) and kept on ice until use. Fluorescence measurements were carried out in a Photon Technology International (PTI, South Brunswick, N.J.) Model RF-F3004 spectrofluorometer with dual emission monochromators using excitation at 350 nm and emission at 400 and 490 nm. The instrument was equipped with a thermostated cuvette holder with stirring capabilities, as well as with a computer-controlled pump which allowed for reagent addition during measurement. Instrument control and data collection was done by PTI's OSCAR software running on an IBM compatible computer. Different concentrations of the test compounds (60 $\mu$L in dimethyl sulfoxide) were added to 5.94 mL of assay buffer containing approximately 3×$10^6$ loaded cells, and 5 $\mu$M nitrendipine (in 30 $\mu$L EtOH) to block L-type $Ca^{2+}$ channels. Samples were incubated for 10 minutes at 30° C. and then aliquoted into three 10×10 mm disposable acrylic cuvettes. Emission signals at 400 and 490 nm were acquired from each cuvette at 30° C. for 50 seconds. At 20 seconds after the start of reading, cells were depolarized by the addition of 160 $\mu$L of stimulation solution (1 M KCl, 68 mM $CaCl_2$) to the cuvette via the computer-controlled pump. Ratio of dual emission signals (400 nm/490 nm), which is proportional to intracellular $Ca^{2+}$ concentration, was plotted against time, and the difference between maximal response after stimulation and basal value (before stimulation) was determined. Values obtained in this way were plotted as a function of drug concentration. $IC_{50}$ values of test compounds were calculated by fitting a 4-parameter logistic function to the data using the least squares method.

In Vivo Biological Protocol

A compound of the present invention was dissolved in water using 10% (weight/volume) Emulphor (GAF Corp., Wayne, N.J.) surfactant. Substances were administered by intravenous injection into the retro-orbital venous sinus. All testing was performed 15 minutes or 45 minutes after drug injection. All the male mice, 3 to 4 weeks old, were obtained from Jackson Laboratories, Bar Harbour, Me. Immediately before anticonvulsant testing, mice were placed upon a wire mesh, 4 inches square suspended from a steel rod. The square was slowly inverted through 180 degree and mice observed for 30 seconds. Any mouse falling from the wire mesh was scored as ataxia.

Mice were placed into an enclosed acrylic plastic chamber (21 cm height, approximately 30 cm diameter) with a high-frequency speaker (4 cm diameter) in the center of the top lid. An audio signal generator (Protek Model B-810) was used to produce a continuous sinusoidal tone that was swept linearly in frequency between 8 kHz and 16 kHz once each 10 msec. The average sound pressure level (SPL) during stimulation was approximately 100 dB at the floor of the chamber. Mice were placed within the chamber and allowed to acclimatize for 1 minute. DBA/2 mice in the vehicle-treated group responded to the sound stimulus (applied until tonic extension occurred, or for a maximum of 60 sec) with a characteristic seizure sequence consisting of wild running followed by clonic seizures, and later by tonic extension, and finally by respiratory arrest and death in 80% or more of the mice. In vehicle-treated mice, the entire sequence of seizures to respiratory arrest lasts approximately 15 to 20 seconds.

The incidence of all the seizure phases in the drug-treated and vehicle-treated mice was recorded, and the occurrence of tonic seizures were used for calculating anticonvulsant $ED_{50}$ values by probit analysis. Mice were used only once for testing at each time and dose point. Results of this assay are shown below in Table 2.

TABLE 1

| | In Vitro Data |
|---|---|
| Example No. | IMR-32 % of Blockade @ $\mu$M |
| 1 | $IC_{50}$ = 0.4 $\mu$M (est.) |
| 2 | $IC_{50}$ = 1.3 $\mu$M (est.) |
| 3 | $IC_{50}$ = 0.77 $\mu$M |
| 4 | $IC_{50}$ = 1.0 $\mu$M (est.) |

TABLE 1-continued

| | In Vitro Data |
|---|---|
| Example No. | IMR-32 % of Blockade @ µM |
| 5 | 97% @ 10, 79% @ 1 |
| 6 | $IC_{50}$ = 1.1 µM |
| 7 | 95% @ 10, 67% @ 1 |
| 8 | $IC_{50}$ = 0.67 µM |
| 9 | 55% @ 10, 11% @ 1 |

TABLE 2

| | In Vivo Data |
|---|---|
| Example No. | DBA/2 mice % protection (dose) |
| 3 | 80% @ 30 mg/kg |
| 4 | 60% @ 30 mg/kg |
| 5 | 100% @ 30 mg/kg |

What is claimed is:

1. Compounds having the Formula I

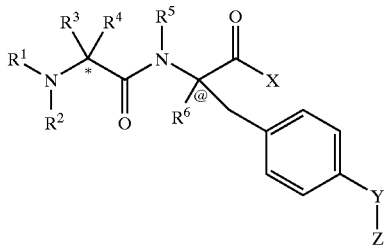

wherein
* denotes a first chiral center when $R^3$ and $R^4$ are different;
@ denotes a second chiral center; $R^1$ and $R^2$ are independently hydrogen, $C_1$–$C_8$ alkyl, $C_3$–$C_7$ cycloalkyl $C_1$–$C_8$ substituted alkyl, $C_1$–$C_6$ alkoxy, hydroxy, $C_3$–$C_7$ cycloalkenyl, $C_3$–$C_7$ substituted cycloalkenyl, $C_3$–$C_7$ substituted cycloalkyl, —$(CH_2)_n$-aryl, —$(CH_2)_n$-substituted aryl, $C_2$–$C_8$ alkenyl, $C_2$–$C_8$ substituted alkenyl, —$(CH_2)_n$-heteroaryl, —$(CH_2)_n$—$C_3$–$C_7$ cycloalkyl, —$(CH_2)_n$-substituted heteroaryl, —$(CH_2)_n$—$C_3$–$C_7$ heterocycloalkyl, —$(CH_2)_n$-substituted $C_3$–$C_7$ heterocycloalkyl, or $R^1$ and $R^2$ may be taken together to form a 5- to 7-membered ring which may contain a heteroatom, provided that $R^1$ and $R^2$ are not both hydrogen;
$R^3$, $R^5$, and $R^6$ are independently hydrogen or $C_1$–$C_8$ alkyl;
$R^4$ is —$(CH_2)_n$-heteroaryl or —$(CH_2)_n$-substituted heteroaryl;
Y is —$(CH_2)_n$—, $O(CH_2)_n$—, —$(CH_2)_nO$—, —$N(R^7)(CH_2)_n$—, —$(CH_2)_nN(R^7)$—, —$S(CH_2)_n$—, —$(CH_2)_nS$—, —C=C—, or —C≡C—;
$R^7$ is hydrogen, methyl or ethyl;
Z is aryl, substituted aryl, heteroaryl, substituted heteroaryl, $C_3$–$C_7$ cycloalkyl, substituted $C_3$–$C_7$ cycloalkyl, $C_1$–$C_8$alkyl, —$C_3$–$C_7$ heterocycle, or -substituted $C_3$–$C_7$ heterocycle;
X is $OR^8$, $NHR^8$, or $NR^8R^9$;
$R^8$ and $R^9$ are independently $C_1$–$C_{12}$alkyl, $C_1$–$C_{12}$ substituted alkyl, —$(CH_2)_n$—$C_3$–$C_8$ heterocycloalkyl, $C_3$–$C_7$ cycloalkyl, substituted $C_3$–$C_7$ cycloalkyl, arylalkyl, substituted arylalkyl, heteroarylalkyl, substituted heteroarylalkyl, or $NR^8R^9$ can together with the nitrogen atom form a ring having from 4 to 7 atoms;
each n is 0 to 5, and the pharmaceutically acceptable salts, esters, amides and prodrugs thereof.

2. A compound according to claim 1 wherein $R^1$ is 3-methylbutyl.

3. A compound according to claim 1 wherein $R^3$, $R^5$, and $R^6$ are hydrogen.

4. A compound according to claim 1 wherein Y is —$OCH_2$—, —$CH_2CH_2$—, or —$NCH_2$—.

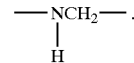

5. A compound according to claim 1 wherein Z is phenyl.
6. A compound according to claim 1 wherein $R^5$ and $R^6$ are hydrogen.
7. A compound according to claim 1 wherein $R^2$ is $C_1$–$C_8$ alkyl, cyclohexyl, substituted cyclohexyl, —$CH_2$-phenyl, or $CH_2$-substituted phenyl.
8. A compound according to claim 1 wherein $R^2$ is $C_3$–$C_7$ cycloalkenyl.
9. The compounds:
N-{1-tert-Butylcarbamoyl-2-[4-(pyridin-3-ylmethoxy)-phenyl]-ethyl}-2-[methyl-(3-methyl-butyl)-amino]-3-pyridin-4-yl-propionamide;
N-[2-(4-Benzylamino-phenyl)-1-tert-butylcarbamoyl-ethyl]-2-[methyl-(3-methyl-butyl)-amino]-3-pyridin-4-yl-propionamide.
10. A pharmaceutical composition comprising a compound of claim 1.
11. A method of treating epilepsy, the method comprising administering to a patient having epilepsy a therapeutically effective amount of a compound of claim 1.

* * * * *